US009207173B2

(12) United States Patent
Li et al.

(10) Patent No.: US 9,207,173 B2
(45) Date of Patent: Dec. 8, 2015

(54) SURFACE PLASMON RESONANCE BASED SENSING DEVICES AND METHODS FOR REAL-TIME ANALYSIS OF ANALYTE SECRETION FROM LIVING CELLS

(71) Applicants: Chenzhong Li, Miami, FL (US); Chang Liu, Miami, FL (US)

(72) Inventors: Chenzhong Li, Miami, FL (US); Chang Liu, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 14/198,814

(22) Filed: Mar. 6, 2014

(65) Prior Publication Data

US 2014/0268159 A1 Sep. 18, 2014

Related U.S. Application Data

(60) Provisional application No. 61/781,232, filed on Mar. 14, 2013.

(51) Int. Cl.
*G01N 21/55* (2014.01)
*G01N 21/552* (2014.01)
*G01N 33/543* (2006.01)

(52) U.S. Cl.
CPC ........ *G01N 21/553* (2013.01); *G01N 33/54373* (2013.01)

(58) Field of Classification Search
CPC .............. G01N 33/6869; G01N 2333/545; G01N 33/53; G01N 2800/24; G01N 33/6857; G01N 33/74; G01N 2333/54; G01N 2500/00; G01N 2800/52; G01N 2800/7028; G01N 33/569; G01N 33/56966; G01N 2333/475
See application file for complete search history.

(56) References Cited

U.S. PATENT DOCUMENTS

2011/0188043 A1* 8/2011 Davidov et al. ............... 356/445

FOREIGN PATENT DOCUMENTS

| EP | 1 739 406 | 1/2007 |
| WO | WO 2011/066097 A1 | 6/2011 |

OTHER PUBLICATIONS

Altintas, Zeynep et al., "Surface Plasmon Resonance based Immunosensor for the Detection of the Cancer biomarker Carcinoembriyonic Antigen," *Talanta*, 2011, 86:377-383.
Beyene, H. T. et al., "Preparation and plasmonic properties of polymer-based composites containing Ag-Au alloy nanoparticles produced by vapor phase co-deposition," *Journal for Material Sciences*, 2010, 45:5865-5871.
Forzani, Erica et al., "Detection of Heavy Metal Ions in Drinking Water Using a High-Resolution Differential Surface Plasmon Resonance Sensor," *Environmental Science & Technology*, 2005, 39:1257-1262.
Folkman, J. "Angiogenesis in cancer, vascular, rheumatoid and other disease,", *Nature Medicine*, 1995, 1(1):27-31.
Hanahan, Douglas et al., "The Hallmarks of Cancer," *Cell*, 2000, 100:57-70.

(Continued)

*Primary Examiner* — Michael P Stafira
(74) *Attorney, Agent, or Firm* — Saliwanchik, Lloyd & Eisenschenk

(57) ABSTRACT

The present invention provides surface plasmon resonance (SPR) based sensing systems and methods for rapid, sensitive, and real-time analysis of analyte secretion from living cells. In one embodiment, the SPR based sensing device of the present invention comprises at least one cell culture module for culturing living cells, wherein the cell culture module is configured so that analytes secreted from the living cells can be released onto a SPR sensing surface.

20 Claims, 3 Drawing Sheets

(56) References Cited

OTHER PUBLICATIONS

Huang, Xianming et al., "Expression of Soluble VEGF Receptor 2 and Characterization of Its Binding by Surface Plasmon Resonance," *Biochemical and Biophysical Research Communications*, 1998, 252:643-648.

Li, Yuan et al., "Detection of Protein Biomarkers using RNA Aptamer Microarrays and Enzymatically Amplified SPR Imaging," *Anal Chem*, 2007, 79(3):1082-1088.

Liu, Chang et al., "Real-time monitoring biomarker expression of carcinoma cells by surface plasmon resonance biosensors," *The Royal Society of Chemistry*, 2012, 48:10389-10391.

Ly, Nguyen et al., "Integrated Label-free protein detection and separation in real time using confined surface plasmon resonance imaging," *Anal Chem*, 2007, 79(6):2546-2551.

Matsumoto, Kiyoshi et al., "Preparation and characterization of a polyclonal antibody from rabbit for detection of trinitrotoluene by a surface plasmon resonance biosensor," *Talanta*, 2005, 68(2):305-311.

Presta, Leonard et al., "Humanization of Anti-Vascular Endothelial Growth Factor Monoclonal Antibody for the Therapy of Solid Tumors and Other Disorders," *Cancer Research*, 1997, 57:4593-4599.

Su, Xiaodi et al., "Comparison of surface plasmon resonance spectroscopy and quartz crystal microbalance techniques for studying DNA assembly and hybridization," *Biosensors and Bioelectronics*, 2005, 21(5):719-726.

Su, Xiaodi et al., "Surface plasmon resonance spectroscopy and quartz crystal microbalance study of streptavidin film structure effects on biotinylated DNA assembly and Target DNA hybridization," *Langmuir*, 2005, 21(1): 348-353.

Taylor, Ad of al., "Quantitative and simultaneous detection of four foodborne bacterial pathogens with multi-channel SPR sensor," *Biosens Bioelectron.*, 2006, 22(5):752-758.

Tiedemann, Bridget et al., "Characterization of the vascular endothelial growth factor-receptor interaction and determination of the recombinant protein by an optical receptor sensor," *Biosens Bioelectron*, 2002, 17:983-991.

\* cited by examiner

SURFACE PLASMON RESONANCE BASED SENSING DEVICES AND METHODS FOR REAL-TIME ANALYSIS OF ANALYTE SECRETION FROM LIVING CELLS

CROSS REFERENCE TO RELATED APPLICATION

The present application claims the benefit of U.S. Provisional Application Ser. No. 61/781,232, filed Mar. 14, 2013, which is hereby incorporated by reference herein in its entirety, including any figures, tables, or drawings.

BACKGROUND OF INVENTION

Surface plasmon resonance (SPR) based biosensing technology is a useful tool for investigating the binding activity between, for example, cells, proteins, DNA, and small inorganic molecules, and has great potential in biorecognition measurements. SPR based biosensors measure changes in refractive index at a plane interface between two media with dielectric constants of opposite signs, a dielectric and a metal (such as gold).

SPR can be excited when a wedge of polarized light is directed towards the glass face of the sensor surface under the condition of total internal reflection. The resonant angle at which a minimal intensity of reflected light occurs is a function of the local refractive index at or near the metal (such as gold) surface. The changes in refractive index closely associate with the adsorption or desorption of molecules from the surface.

Analysis of biomarker secretion from living cells has useful clinical, medical, and biochemical applications. Biomarker based technology can, for example, provide molecular-based, individualized cancer diagnosis and treatment. Biomarker based cancer therapy can also have reduced side effects when compared to traditional antineoplastic solutions, such as chemotherapy, radiation therapy, and cryosurgery.

Proteomic biomarkers are involved in many types of cancer. Cancer cells rely on vessel growth to provide a constant supply of oxygen and nutrients to maintain tumor growth and cellular activity. Vascular endothelial growth factor (VEGF), which binds to specialized receptors on the surface of endothelial cells, is a widely studied angiogenic signal protein biomarker produced by oxygen-hungry cells to promote the growth of blood vessels. Some types of tumor cells produce abnormally large amounts of VEGF or block the action of angiogenesis inhibitors. This action, termed as "angiogenic switch," is essential for metastasis of tumor cells.

Existing SPR based sensing platforms can only detect analytes (such as biomarker proteins) in prepared samples, and thus, have certain limitations. For instance, to perform cellular exocytosis and cellular signaling pathways studies, existing SPR based technology usually requires the collection of analytes from cell culture media as well as purification and pretreatment of analytes. These procedures are not only time-consuming, but can also introduce errors into the experiments. Therefore, improved methods for direct measurement of analyte secretion from living cells are needed.

BRIEF SUMMARY

The present invention provides surface plasmon resonance (SPR) based sensing systems and methods for rapid, sensitive, and real-time analysis of analyte secretion from living cells.

In one embodiment, the present invention provides a SPR based sensing device comprising:
a SPR sensing surface capable of generating SPR upon stimulation by incident light, and
a cell culture module for culturing living cells, wherein the cell culture module is configured so that analytes secreted from the living cells can be released onto the SPR sensing surface.

In one embodiment, the SPR sensing surface comprises a metallic layer. In a specific embodiment, the SPR sensing surface comprises gold, or preferably, comprises a thin layer of gold. In one embodiment of the SPR sensing surface, the gold surface layer is adhered to a support layer that comprises glass.

In one embodiment, the present invention provides an in situ SPR based sensing device for real-time analysis of analyte secretion from living cells. In a specific embodiment, the SPR based biosensing device comprises therein a cell culture module. Unlike traditional configurations of SPR systems for biomarker detection, in one embodiment of the present invention, living cells are cultured on the ceiling of a customized SPR flow cell chamber, and biomarker secretion from the living cells is rapidly monitored by an SPR sensing device.

In a further embodiment, the present invention provides a method of real-time analysis of analyte secretion from living cells, wherein the method comprises:
(i) providing a SPR based sensing device comprising:
an SPR sensing surface capable of generating SPR upon stimulation by incident light, and
a cell culture module for culturing living cells, wherein the cell culture module is configured so that analytes secreted from living cells can be released onto the SPR sensing surface;
(ii) culturing living cells in the cell culture module; and
(iii) determining secretion of an analyte of interest from the living cells.

DETAILED DISCLOSURE

The present invention provides surface plasmon resonance (SPR) based sensing systems and methods for rapid, sensitive, and real-time analysis of analyte secretion from living cells.

In one embodiment, the present invention provides a SPR based sensing device comprising:

a SPR sensing surface capable of generating SPR upon stimulation by incident light, and a cell culture module for culturing living cells, wherein the cell culture module is configured so that analytes secreted from the living cells can be released onto the SPR sensing surface.

Figure 1:
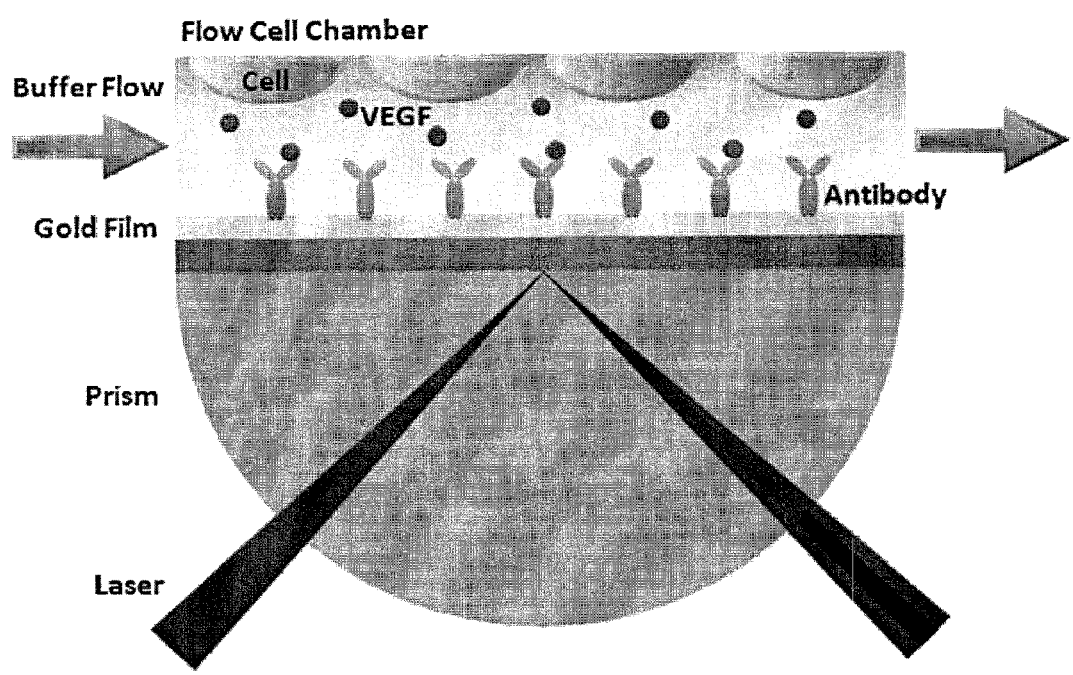
FIG. 1 shows an embodiment of the SPR based biosensor of the present invention. The SPR based biosensor comprises a mini cell culture module for direct measurement of biomarker secretion from living cells.

In one embodiment, the present invention provides an in situ SPR based sensing device for real-time analysis of analyte (such as VEGF) secretion from living cells. In a specific embodiment, the SPR based biosensing device comprises therein a mini cell culture module. Unlike the traditional configuration of SPR systems for biomarker detection, in one embodiment of the present invention, living cells are cultured on the ceiling of a customized SPR flow cell chamber, and biomarker secretion from the living cells is rapidly monitored by a SPR sensing device (FIG. 1).

As shown in the Example, the SPR based sensing device of the present invention can provide real-time analysis of analyte secretion from living cells. Specifically, to test SPR sensor performance and to determine reproducibility and linearity of a gold sensing surface, VEGF samples at various concentrations (0.25, 0.5, 0.75 and 1 µg/mL) were added to a SPR biosensor. The maximum value of the inter-assay relative standard deviations is 13.6% (n=4), indicating acceptable reproducibility. In addition, a direct measurement of VEGF secretion from living carcinoma cells was performed. SKOV-3 cells were cultured for 48 hr on gelatin coated SPR flow chamber before tests. According to the calibration curve for VEGF samples at various concentrations, SKOV-3 cells released about 1 µg/mL/cell VEGF during the experiment.

Advantageously, the SPR sensing devices and methods of the present invention can mimic the in vivo microenvironment of cell signaling pathways, and can be used for the detection and analysis of biomarker secretion from living cells and tissues.

Applications of the SPR based sensing devices and methods of the present invention also include, but are not limited to, determining the presence and/or level of analyte secretion from living cells; determining functions of analyte (such as protein) binding activity, preferably, in living cells; identifying binding partners to target analyte molecules; elucidating cell signaling pathways, preferably, in living cells; and identifying disease biomarkers in clinical samples.

Surface Plasmon Resonance Based Sensing Device

In one embodiment, the present invention provides a surface plasmon resonance (SPR) based sensing device for real-time analysis of analyte secretion from living cells, wherein the device comprises:

a SPR sensing surface capable of generating SPR upon stimulation by incident light; and a cell culture module for culturing living cells, wherein the cell culture module is configured so that analytes secreted from the living cells can be released onto the SPR sensing surface.

Thus, the SPR sensing device can comprise one or more SPR sensing surfaces and/or one or more cell culture modules.

In one embodiment, the SPR sensing surface comprises a metallic surface. In certain embodiments, the metallic surface comprises one or more metals selected from, for example, gold, silver, copper, platinum, aluminum, tin, zinc, tantalum, magnesium, nickel, palladium, cobalt, molybdenum, iron, titanium, chromium, and alloys comprising one or more aforementioned metals. In one embodiment, the metallic surface comprises gold, or preferably, a thin layer of gold.

In certain embodiments, the metallic surface is provided in the form of a thin metallic layer, such as a thin layer having a thickness of 0.01 nm to 10 µm, or any value therebetween.

In one embodiment of the SPR sensing surface, the metallic surface layer is adhered to a support layer capable of transmitting light. In one embodiment, the support layer is, or comprises, glass. In one embodiment, the support layer is flat or substantially flat. In one embodiment, the metallic surface layer is flat or substantially flat.

The SPR based sensing device can further comprise: a binding partner that binds to an analyte of interest secreted from living cells, wherein the SPR sensing surface is coated with the binding partner. In one embodiment, the binding partner binds specifically to an analyte of interest. In one embodiment, the SPR sensing surface is coated with binding partners of an analyte of interest. In one embodiment, the binding partner is bound or affixed to the SPR sensing surface, such as via a covalent bond or hydrogen bond.

The SPR sensing surface (for example, the metallic surface layer) can be modified with, or comprise chemical linkers and/or spacer molecules, such as, carboxylic acid groups, poly(lysine), and dextran. In one embodiment, the metallic surface layer of the SPR sensing surface is modified with, or comprises, a carboxymethylated dextran layer to create a hydrophilic environment.

The SPR based sensing device can comprise more than one cell culture module. In one embodiment, the cell culture module is mounted above the SPR sensing surface.

In one embodiment, the cell culture module comprises a carrier for supporting living cells. In one embodiment, the cell culture module, which comprises the carrier for supporting living cells, can be controllably sealed to hold the living cells in its inner space.

In one specific embodiment, the cell culture module is, or is part of, a flow cell chamber.

The carrier for supporting living cells can be, for example, a tissue culture plate, tissue culture well, or the gasket of a flow cell chamber.

In certain embodiments, the cell culture module comprises one or more controllers configured to control cell culture conditions such as, for example, medium flow, temperature, humidity, gas exchange, pH, $CO_2$ level, $O_2$ level, pressure, and light. In certain embodiments, the cell culture module comprises one or more sensors configured to detect factors, such as, for example, cell viability, cell count, cell activity, cell metabolite level, level of nutrients (such as glucose, electrolytes (e.g., $K^+$, $Ca^{2+}$, $Na^+$), medium flow, temperature, humidity, gas exchange, pH, $CO_2$ level, $O_2$ level, pressure, and light.

In certain embodiments, the cell culture device further comprises one or more pumps, valves, and/or flow channels to provide a constant inflow of gas and/or fluids, such as water, buffers, culture medium, analytes, nutrients, and washes. In another embodiment, the cell culture device further comprises one or more fluid circulation channels. In one embodiment, the fluid circulation channel fills fluids into the inner space of the cell culture module and circulates the gas and/or liquid. In one embodiment, the fluid circulation channel is configured to provide unidirectional flow of gas and/or liquid.

The carrier for supporting living cells and/or the cell culture module can be made of, or comprise, materials including, but not limited to, polydimethylsiloxane (PDMS), glass ceramics, glass, ceramics, silica, titania, zirconia, alumina, hydroxyapatite, metal oxides, and a combination thereof.

The term "culturing," as used herein, refers to incubating a cell and/or microorganism or a plurality thereof under conditions wherein the cell and/or microorganism or plurality thereof can perform some, if not all, biological processes, such as, for example, growth, reproduction, transcription, translation, and metabolism. For example, a cell or a microorganism that is cultured may be growing or reproducing. In a preferred embodiment, living cells and/or living microorganisms are cultured.

The SPR based sensing device can be used to analyze secretions of any living cells, as well as unicellular and multicellular microorganisms. Living cells whose secretion can be analyzed in accordance with the present invention can be of any species, including, but are not limited to, plants; animals, including, but not limited to, chimpanzees, orangutans, humans, monkeys, fish, amphibians, reptiles, rabbits, dogs, cats, horses, cattle, pigs, sheep, goats, chickens, mice, rats, guinea pigs, and hamsters; fungi; bacteria; viruses; and protozoans. Living cells whose secretion can be analyzed in accordance with the present invention can be of any types of tissues or organs, including, but not limited to, connective, muscle, epithelial, neural; cardiac, breast, esophagus, brain, lung, blood, immune, stomach, liver, gallbladder, pancreas, intestine, colon, kidney, bladder, prostate, uterus, rectum, and skin cells. Living cells whose secretion can be analyzed in accordance with the present invention can be benign or malignant tumor cells.

In one embodiment, the SPR based sensing device further comprises a light source configured to illuminate the SPR sensing surface. The term "light," as used herein, includes visible and non-visible light. The light source can emit light including, for example, violet, blue, green, yellow, orange, red, far-red, ultraviolet light (such as ultraviolet A, ultraviolet B, ultraviolet C), X-rays, and infrared spectral ranges.

Light sources for illuminating the SPR sensing surface include, but are not limited to, laser light sources, such as helium neon laser or other suitable laser; an incandescent light; a light emitting diode (LED); an organic light-emitting diode (OLED); an organic luminescent diode; a light oscillator; a light source configured to emit a filtered, collimated light; and a light source configured to emit a monochromatic light.

In certain embodiments, the light source is configured to emit light having a wavelength within the range of 50 nm to 1,000 nm, or any range or wavelength therebetween, such as between 350 nm to 500 nm.

In certain embodiments, the light source comprises a light polarization control means. Suitable light polarization control means include, but are not limited to, polaroid, Glan prism, polarizing beam splitter, or any combination thereof.

In one embodiment, the SPR based sensing device further comprises an optical detector for measuring the reflectivity of the light by the SPR sensing surface.

In one embodiment, the SPR based device further comprises, or is connected to, a computer processing system or network. In certain embodiments, the computer process system or network can perform functions including, but not limited to, controlling the output of the light source, measuring the reflectivity of the light detected by the detector, transmitting and/or processing data, and/or performing data analysis.

In one embodiment, the controlling device comprises a software code that can be stored on one or more computer-readable media (e.g., non-transitory computer-readable media). When a data-processing system or apparatus reads and executes the code and/or data stored on a machine-readable medium, the data-processing system or apparatus system performs the methods and processes embodied as the software code stored within the machine-readable medium.

In one embodiment, the present invention provides an array comprising an SPR based sensing device of the present invention.

Binding Partners of Analytes

In certain embodiments, the SPR based sensing device is capable of real-time analysis of analyte secretion from living cells. Analytes that can be analyzed using the SPR sensing apparatus include, but are not limited to, nucleic acids (such as, single and double-stranded oligonucleotides, DNA, RNA); proteins, protein fragments, amino acids peptides, antibodies, antigens; carbohydrates; lipids; inorganic compounds; cellular components including, but not limited to, cell surface molecules, metabolites; viruses and virus fragments; and other organic compounds including, but not limited to, hormones and vitamins.

In certain embodiments, the analyte binding partners include, but are not limited to, antibodies that bind (preferably, bind specifically) to a protein or peptide analyte of interest; nucleic acid molecules that hybridize (preferably, under stringent conditions) to a nucleic acid analyte of interest; aptamers that bind (preferably, bind specifically) to an analyte of interest; receptors that bind (preferably, bind specifically) to an antigen analyte of interest; and antigens that bind (preferably, bind specifically) to a receptor analyte of interest.

In certain embodiments, the SPR sensing apparatus is capable of real-time analysis of biomarker protein secretion from living cells. Biomarker proteins that can be analyzed in accordance with the present invention include, but are not limited to, growth factors such as vascular endothelial growth factors (e.g., VEGF-A, VEGF-B, VEGF-C, VEGF-D), placental growth factor (PGF), adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF), neurotrophins, platelet-derived growth factor (PDGF), thrombopoietin (TPO), transforming growth factor alpha (TGF-$\alpha$), transforming growth factor beta (TGF-$\beta$), tumor necrosis factor-alpha (TNF-$\alpha$); Myc, TNF-$\alpha$; COX-2, prostaglandin (e.g., PEG2), interferons such as Interferon-beta (IFN-$\beta$), Interferon-alpha (IFN-$\alpha$) which includes IFN-$\alpha$ subtypes such as IFNA1, 2 and 8, and Interferon-gamma (IFN-$\gamma$); p38K; IRF3; the interleukin family such as Interleukin-1 (IL-1), interleukin-1 beta (IL-1$\beta$), Interleukin-2 (IL-2), Interleukin-3 (IL-3), Interleukin-4 (IL-4), Interleukin-5 (IL-5), Interleukin-6 (IL-6), Interleukin-7 (IL-7), Interleukin-8 (IL-8), Interleukin-9 (IL-9), Interleukin-10 (IL-10), Interleukin-11 (IL-11), Interleukin-12 (IL-12), Interleukin-13 (IL-13), Interleukin-14 (IL-14), Interleukin-15 (IL-15), Interleukin-16 (IL-16), Interleukin-17 (IL-17), Interleukin-18 (IL-18), Interleukin-19 (IL-19), Interleukin-20 (IL-20), Interleukin-21 (IL-21), Interleukin-22 (IL-22), Interleukin-23 (IL-23), Interleukin-24 (IL-24), Interleukin-25 (IL-25), Interleukin-26 (IL-26), Interleukin-27 (IL-27), Interleukin-28 (IL-28), Interleukin-29 (IL-29), Interleukin-30 (IL-30), Interleukin-31 (IL-31), Interleukin-32 (IL-32), Interleukin-33 (IL-33), Interleukin-34 (IL-34), Interleukin-35 (IL-35); the interleukin receptor family; the macrophage inflammatory protein family such as macrophage inflammatory protein 2 (MIP-2) and macrophage inflammatory protein 1$\alpha$ (MIP-1

α); macrophage colony-stimulating factor (M-CSF); monocyte chemotactic protein-1 (MCP-1); and immunoglobulins such as IgA, IgG; IgM, IgD, and IgE.

In certain embodiments, protein analyte binding partners include, but are not limited to, antibodies that bind to, or bind specifically to, a protein or peptide analyte of interest.

An antibody that is contemplated for use in the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', $F(ab')_2$ and Fv fragments.

As used herein, "antigen binding fragment" with respect to antibodies, refers to, for example, Fv, F(ab) and $F(ab')_2$ fragments.

"Specific binding" or "specificity" refers to the ability of an antibody or other agent to detectably bind an epitope presented on an antigen of interest, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules.

In certain embodiments, analyte binding partners include nucleic acid molecules that hybridize, under stringent conditions, with a nucleic acid analyte.

In one embodiment, the sensing surface is coated with nucleic acid molecules complementary to the full length, or a fragment of, a nucleic acid analyte of interest.

As used herein, "stringent" conditions for hybridization refers to conditions whereby hybridization is typically carried out overnight at 20-25° C. below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$$Tm=81.5\ C+16.6\ \mathrm{Log}\ [Na+]+0.41(\%\ G+C)-0.61(\%\ \mathrm{formamide})-600/\mathrm{length\ of\ duplex\ in\ base\ pairs.}$$

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

Real-time Analysis of Analyte Secretion from Living Cells

In one embodiment, the present invention provides uses of the SPR based sensing device for real-time analysis of analyte secretion from living cells. In one embodiment, the present invention provides a method of real-time analysis of analyte secretion from living cells, wherein the method comprises:

providing a SPR based sensing device comprising:

an SPR sensing surface capable of generating SPR upon stimulation by incident light, and a cell culture module for culturing living cells, wherein the cell culture module is configured so that analytes secreted from living cells can be released onto the SPR sensing surface;

culturing living cells in the cell culture module; and determining secretion of an analyte of interest from the living cells.

The method of real-time analysis of analyte secretion from living cells can further comprise: coating the SPR sensing surface with at least one binding partner to the analyte of interest.

EXAMPLE

Following is an example that illustrates embodiments and procedures for practicing the invention. This example should not be construed as limiting.

Example 1

Real-Time Analysis of VEGF Secretion from Living Cells

This Example shows that the SPR based biosensor of the present invention can provide sensitive, rapid, and real-time detection and analysis of biomarkers from living cells.

Initially, to determine sensor performance as well as reproducibility and linearity of the functionalized gold sensing surface, VEGF samples at various concentrations (0.25, 0.5, 1, 1.5, 2, 2.5, 3, 4 mg mL$^{-1}$) are added to a SPR biosensor.

Briefly, carboxylic acid groups are immobilized on the sensing surface and activated in the SPR microfluidic system using a method reported in Su et al. (2005), which is hereby incorporated by reference in its entirety. The activated SPR chip is immobilized by injecting 50 mg mL$^{-1}$ protein G solution to capture the Fc portions of the antibody to assure proper antibody orientation. 50 mg mL$^{-1}$ monoclonal anti-VEGF antibody, which is the biorecognition ligand, is added to the top of the protein G layer. All injections to the SPR microfluidic system are performed at a 20 ml min$^{-1}$ rate. SPR experiments are performed using phosphate buffered saline (PBS) as the flowing buffer, and all solutions are prepared in PBS (pH=7.4) unless otherwise specified.

Figure 2A:
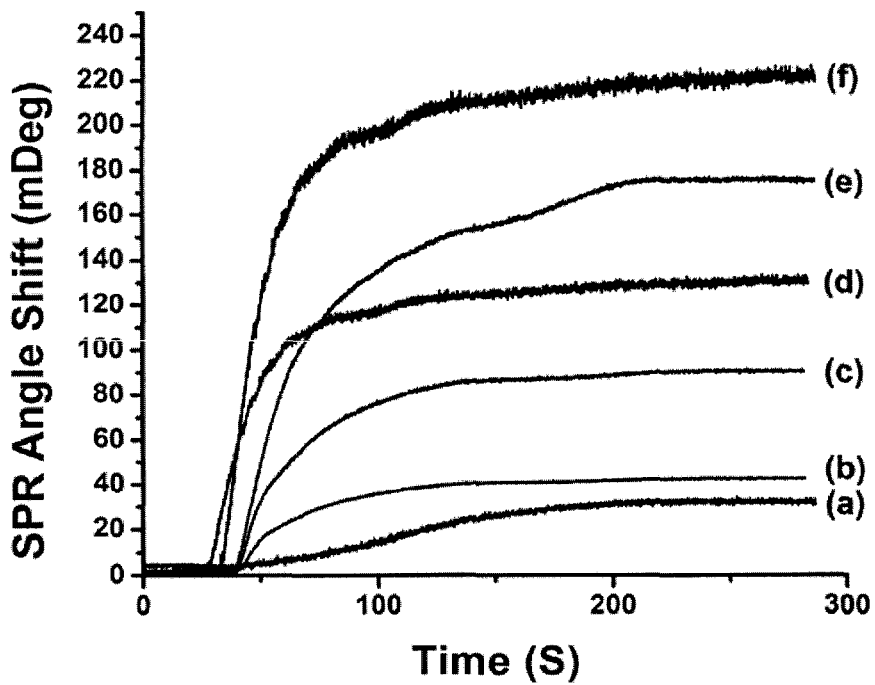
FIG. 2A shows SPR sensor responses to VEGF samples at different concentration levels (a) at 0.25 μg mL$^{-1}$, (b) at 0.5 μg mL$^{-1}$, (c) at 1.0 μg mL$^{-1}$, (d) at 1.5 μg mL$^{-1}$, (e) at 2.0 μg mL$^{-1}$, and (f) at 2.5 μg mL$^{-1}$.
Figure 2B:
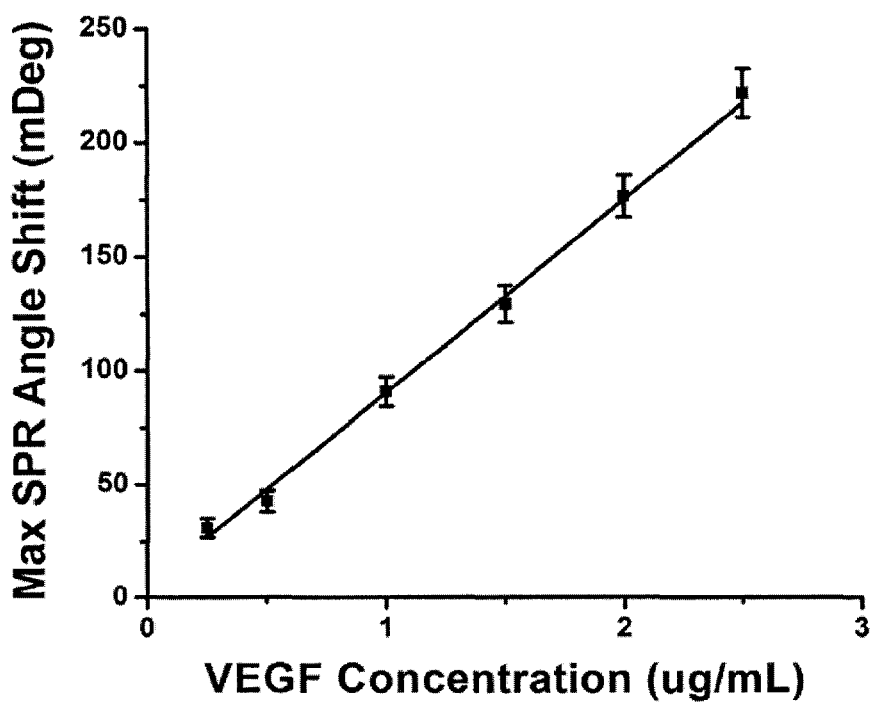
FIG. 2B depicts the calibration curve obtained by a linear fit of SPR responses to different concentrations of VEGF samples.

FIG. 2A shows the time resolved SPR spectra in response to VEGF binding (3, 4 mg mL$^{-1}$ samples not shown). VEGF binding is characterized by the SPR angle shift upon introduction of the VEGF sample solution. FIG. 2B depicts the calibration curve obtained by a linear fit of SPR responses to VEGF samples with different concentrations. The SPR sensor detects VEGF within a linear dynamic range of 0.1-2.5 mg mL$^{-1}$. The maximum value of the inter-assay relative standard derivations is 13.6% (n=4).

In addition, VEGF secretion from living cancer cells is determined using a SPR based biosensor comprising a cell culture system in the flow cell chamber.

Initially, cell viability is examined in a SPR flow chamber. After the polydimethylsiloxane (PDMS) chamber gasket (Biosensing Instrument Inc.) is detached from the SPR flow chamber, drops of 0.1% w/v gelatin solution are applied onto the PDMS gasket to cover the entire surface. The gasket is then dried for 12 h in a biological fume hood to prevent contamination.

Human ovarian carcinoma SKOV-3 cells are cultured on the gelatin coated gasket in McCoy's 5A medium added with 1% penicillin and 10% fetal bovine serum, and are maintained in a 37° C. cell incubator with a humidified atmosphere of 5% $CO_2$ and 95% air. After 48 h incubation, SKOV-3 cells are stained with MitoTracker Red CMXRos dye (579/599 nm) and Hoechst 33342 dye (350/461 nm). SKOV cells cultured on PDMS gasket not coated with gelatin and SKOV cells cultured on a tissue culture plate are control experiments. Fluorescent imaging is performed to examine cell confluency on each substrate. The cell counts on the tissue culture plate, gelatin coated gasket, and uncoated gasket are 174, 218, and 76, respectively. Since the gelatin coated gasket provides significant enhancement of cell attachment when compared to the uncoated gasket, gelatin is a suitable substrate for the living cell experiment in the SPR flow chamber.

To directly measure of the level of VEGF secreted from living carcinoma cells, SKOV-3 cells are cultured for 48 h on gelatin coated gaskets, and the SPR sensing chip is functionalized using monoclonal anti-VEGF antibody. The PDMS flow chamber gasket coated with SKOV-3 cell culture is removed from cell culture medium and thoroughly rinsed with Kreb's buffer to remove cell culture medium and unattached cells. The PDMS gasket bound with SKOV-3 cells is mounted on the SPR flow chamber, and SPR flowing buffer is changed from PBS (pH=7.4) to Kreb's buffer (pH=7.4) to maintain cell viability during experiments. After resuming the buffer flow, 500 mm $Ca^{2+}$ ionophore (A22187) is injected to induce rapid exocytosis, thereby releasing VEGF from SKOV-3 cells.

Figure 3A:
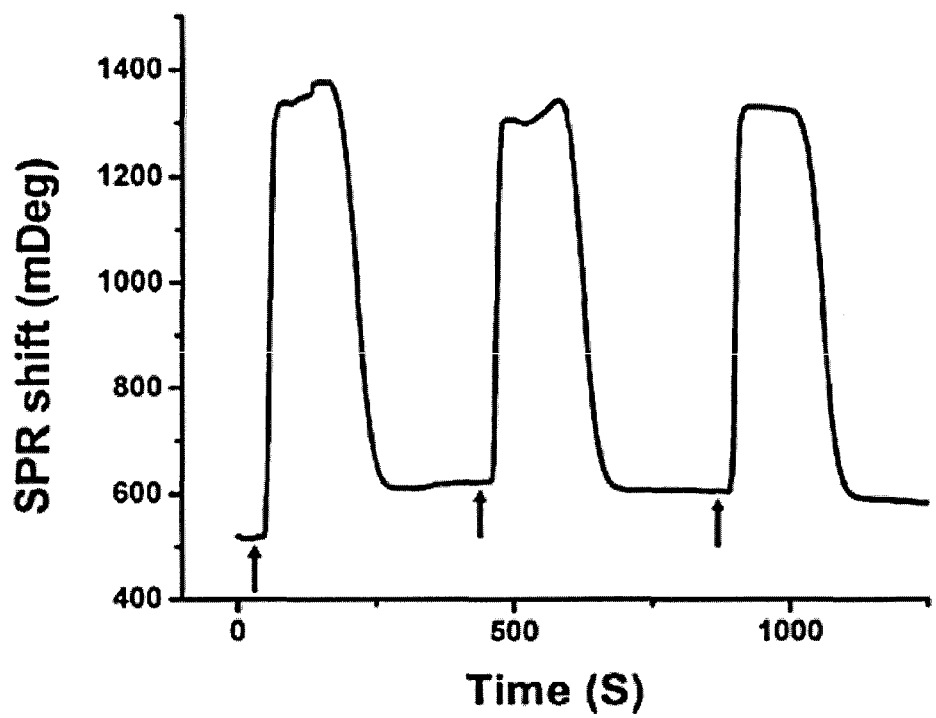
FIG. 3A shows SPR sensor responses to living SKOV-3 cell secretion stimulated by injections of 500 μm Ca$^{2+}$ inophore (A23187). Each arrow indicates an injection of Ca$^{2+}$ inophore.

FIG. 3A shows the time resolved SPR responses upon $Ca^{2+}$ ionophore injections. Each arrow in FIG. 3A indicates an injection of $Ca^{2+}$ ionophore. An 87±6 mDeg SPR angle shift is observed after the first injection. The second and third injections do not induce identifiable angle shift, indicating that all intracellular VEGF has been released during the first stimulation. The calibration curve for VEGF samples at different concentrations show that SKOV-3 cells release about 1 mg $mL^{-1}$ VEGF during the stimulation.

In addition, the average amount of VEGF released per cell is examined. SKOV cells at different concentrations ($5 \times 10^4$, $10 \times 10^4$, $20 \times 10^4$) are seeded on three similar PDMS gaskets and cultured under the same conditions. After 48 h, the cell numbers reached $8 \times 10^4$, $16 \times 10^4$, and $32 \times 10^4$, respectively. SPR measurements are then performed on three samples with different cell numbers.

Figure 3B:
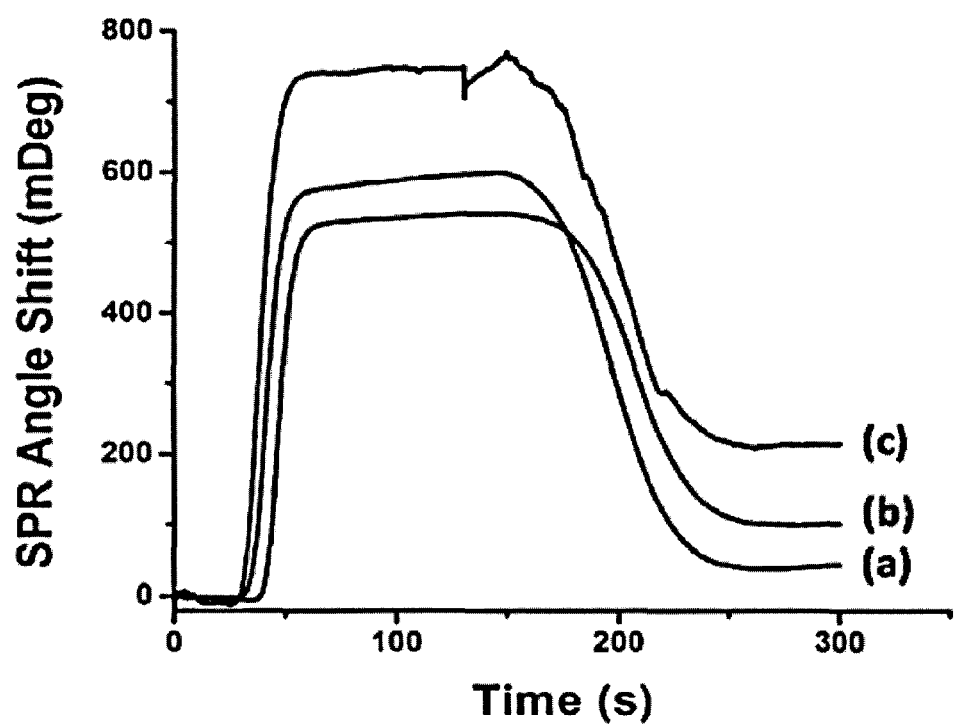
FIG. 3B shows SPR sensor responses to stimulated VEGF secretion from groups of cells with different cell numbers. (a) VEGF secretion from 8×10$^4$ cells induces 43.4 mDeg SPR angle shift; (b) VEGF secretion from 16×10$^4$ cells induces 100.6 mDeg SPR angle shift; (c) VEGF secretion from 32×10$^4$ cells induces 214.2 mDeg SPR angle shift.

FIG. 3B shows the SPR responses to $Ca^{2+}$ induced VEGF secretion from SKOV-3 cells at different concentrations. Based on the VEGF concentration detected by SPR, the cell number and the flow chamber volume (2 mL), the average amount of VEGF released from a single cell is determined as 0.0137±0.0012 pg. The results show that due to the capacity limitation of the SPR flow chamber used in the experiment, the sample with $32 \times 10^4$ cells reaches 100% confluency.

The results show that the SPR based biosensor of the present invention, which comprises a cell culture system, can provide direct, sensitive, and rapid determination of biomarker (such as VEGF) secretion from living cells.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCE

Su et al. Langmuir (2005) 21, 348.

We claim:

1. A surface plasmon resonance (SPR) based sensing device for real-time analysis of one or more analytes secreted from living cells, wherein the device comprises:
   a SPR sensing surface capable of generating SPR upon stimulation by incident light; and
   a cell culture module for culturing living cells, wherein the cell culture module is configured such that the culturing of living cells take place spaced apart from SPR sensing surface and at least one analyte secreted from the living cells falls onto the SPR sensing surface to be sensed by the SPR sensing surface.

2. The device according to claim 1, wherein the cell culture module is, or is part of, a flow cell chamber.

3. The device according to claim 1, wherein the SPR sensing surface comprises a metallic surface.

4. The device according to claim 1, wherein the SPR sensing surface comprises gold.

5. The device according to claim 3, wherein the metallic surface is adhered to a support layer comprising glass.

6. The device according to claim 1, further comprising a binding partner that binds to an analyte of interest secreted from living cells, wherein the SPR sensing surface is coated with the binding partner.

7. The device according to claim 6, wherein the binding partner binds specifically to a protein or peptide analyte of interest.

8. The device according to claim 7, wherein the binding partner is an antibody or aptamer that binds specifically to a protein or a peptide analyte of interest.

9. The device according to claim 6, wherein the binding partner is a nucleic acid molecule that hybridizes under stringent condition, or an aptamer that binds specifically, to a nucleic acid analyte of interest.

10. A method of real-time analysis of one or more analytes secreted from living cells, wherein the method comprises:
    providing a SPR based sensing device wherein the device comprises:
    an SPR sensing surface capable of generating SPR upon stimulation by incident light; and
    a cell culture module for culturing living cells, wherein the cell culture module is configured such that the culturing of living cells takes place spaced apart from the SPR sensing surface and at least one analyte secreted from living cells falls onto the SPR sensing surface to be sensed by the SPR sensing surface, and
    wherein the method further comprises:
    culturing living cells in the cell culture module and spaced apart from the SPR sensing surface; and
    determining secretion of an analyte of interest from the living cells.

11. The method according to claim 10, wherein the SPR sensing surface is provided under the cell culture module and opposite to a ceiling thereof, and wherein the culturing of living cells in the cell culture module takes place on the ceiling of the cell culture module.

12. The method according to claim 10, wherein the cell culture module comprises at least one controller configured to control cell culture conditions within the cell culture module, wherein the cell culture conditions include at least one of temperature, carbon dioxide ($CO_2$) level, and oxygen ($O_2$) level.

13. The method according to claim 10, wherein the cell culture module comprises at least one controller configured to control cell culture conditions within the cell culture module, wherein the cell culture conditions include temperature, $CO_2$ level, and $O_2$ level.

14. The method according to claim 10, wherein the analyte of interest is vascular endothelial growth factors (VEGF) secreted from the living cells.

15. The method according to claim 10, wherein the analyte of interest is VEGF-A, VEGF-B, VEGF-C, VEGF-D, placental growth factor (PGF), adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), tumor necrosis factor-alpha (TNF-α); Myc, TNF-α; COX-2, prostaglandin (e.g., PEG2), Interferon-beta (IFN-β), Interferon-alpha (IFN-α), and Interferon-gamma (IFN-γ), p38K; IRF3, Interleukin-1 (IL-1), Interleukin-1 beta (IL-1β), Interleukin-2 (IL-2), Interleukin-3 (IL-3), Interleukin-4 (IL-4), Interleukin-5 (IL-5), Interleukin-6 (IL-6), Interleukin-7 (IL-7), Interleukin-8 (IL-8), Interleukin-9 (IL-9), Interleukin-10 (IL-10), Interleukin-11 (IL-11), Interleukin-12 (IL-12), Interleukin-13 (IL-13), Interleukin-14 (IL-14), Interleukin-15 (IL-15), Interleukin-16 (IL-16), Interleukin-17 (IL-17), Interleukin-18 (IL-18), Interleukin-19 (IL-19), Interleukin-20 (IL-20), Interleukin-21 (IL-21), Interleukin-22 (IL-22), Interleukin-23 (IL-23), Interleukin-24 (IL-24), Interleukin-25 (IL-25), Interleukin-26 (IL-26), Interleukin-27 (IL-27), Interleukin-28 (IL-28), Interleukin-29 (IL-29), Interleukin-30 (IL-30), Interleukin-31 (IL-31), Interleukin-32 (IL-32), Interleukin-33 (IL-33), Interleukin-34 (IL-34), Interleukin-35 (IL-35), an interleukin receptor, a macrophage inflammatory protein, macrophage colony-stimulating factor (M-CSF), monocyte chemotactic protein-1 (MCP-1), or an immunoglobulin.

16. The device according to claim 1, wherein the cell culture module is configured such that the culturing of living cells takes place on a ceiling of the cell culture module, and wherein the SPR sensing surface is provided under the cell culture module and opposite to the ceiling thereof.

17. The device according to claim 1, wherein the cell culture module comprises at least one controller configured to control cell culture conditions within the cell culture module, wherein the cell culture conditions include at least one of temperature, carbon dioxide ($CO_2$) level, and oxygen ($O_2$) level.

18. The device according to claim 1, wherein the cell culture module comprises at least one controller configured to control cell culture conditions within the cell culture module, wherein the cell culture conditions include temperature, $CO_2$ level, and $O_2$ level.

19. The device according to claim 1, wherein the at least one analyte, on which the device is configured to perform real-time analysis, is vascular endothelial growth factors (VEGF) secreted from living cells.

20. The device, according to claim 1, wherein the at least one analyte, on which the device is configured to perform real-time analysis, is at least one of VEGF-A, VEGF-B, VEGF-C, VEGF-D, placental growth factor (PGF), adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), tumor necrosis factor-alpha (TNF-α); Myc, TNF-α; COX-2, prostaglandin (e.g., PEG2), Interferon-beta (IFN-β), Interferon-alpha (IFN-α), and Interferon-gamma (IFN-γ), p38K; IRF3, Interleukin-1 (IL-1), Interleukin-1 beta (IL-1β), Interleukin-2 (IL-2), Interleukin-3 (IL-3), Interleukin-4 (IL-4), Interleukin-5 (IL-5), Interleukin-6 (IL-6), Interleukin-7(IL-7), Interleukin-8 (IL-8), Interleukin-9 (IL-9), Interleukin-10 (IL-10), Interleukin-11 (IL-11), Interleukin-12 (IL-12), Interleukin-13 (IL-13), Interleukin-14 (IL-14), Interleukin-15 (IL-15), Interleukin-16 (IL-16), Interleukin-17 (IL-17), Interleukin-18 (IL-18), Interleukin-19 (IL-19), Interleukin-20 (IL-20), Interleukin-21 (IL-21), Interleukin-22 (IL-22), Interleukin-23 (IL-23), Interleukin-24 (IL-24), Interleukin-25 (IL-25), Interleukin-26 (IL-26), Interleukin-27 (IL-27), Interleukin-28 (IL-28), Interleukin-29 (IL-29), Interleukin-30 (IL-30), Interleukin-31 (IL-31), Interleukin-32 (IL-32), Interleukin-33 (IL-33), Interleukin-34 (IL-34), Interleukin-35 (IL-35), an interleukin receptor, a macrophage inflammatory protein, macrophage colony-stimulating factor (M-CSF), monocyte chemotactic protein-1 (MCP-1), or an immunoglobulin.

\* \* \* \* \*